US00PP23675P2

(12) United States Plant Patent
Gray

(10) Patent No.: US PP23,675 P2
(45) Date of Patent: Jun. 18, 2013

(54) ***HYDRANGEA* PLANT NAMED 'COTTON CANDY TWO'**

(50) Latin Name: *Hydrangea macrophylla*
Varietal Denomination: Cotton Candy Two

(76) Inventor: Joseph Gray, Davis, CA (US)

( * ) Notice: Subject to any disclaimer, the term of this patent is extended or adjusted under 35 U.S.C. 154(b) by 76 days.

(21) Appl. No.: 13/317,951

(22) Filed: Nov. 1, 2011

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Annette Para
(74) *Attorney, Agent, or Firm* — Penny J. Aguirre

(57) ABSTRACT

A new cultivar of *Hydrangea macrophylla* named 'Cotton Candy Two' that is characterized by its remontant (re-blooming) habit, blooming from May until frost, its lacecap type inflorescences with single sterile flowers surrounding a mass of fertile flowers, its flowers that are dark pink in color in color when grown with a soil PH of 7 or above, its sterile flowers with sepals that have serrated to crenated margins with a fine white edge on most sepals, and its 95% cutting rooting rate.

2 Drawing Sheets

Botanical classification: *Hydrangea macrophylla.*
Varietal denomination: 'Cotton Candy Two'.

CROSS REFERENCE TO A RELATED APPLICATION

This application is co-pending with a U.S. Plant Patent Application filed 'Dancing Butterflies Improved' (U.S. Plant patent application Ser. No. 13/317,953).

BACKGROUND OF THE INVENTION

The present invention relates to a new and distinct cultivar of *Hydrangea macrophylla* and will be referred to hereafter by its cultivar name, 'Cotton Candy Two'. 'Cotton Candy Two' represents a new lacecap type *Hydrangea*, a deciduous shrub grown for landscape use and for use as a potted plant.

'Cotton Candy Two' originated as a seedling that arose from seed planted from open pollination of *Hydrangea macrophylla* 'Frau Reiko' (U.S. Plant Pat. No. 9,500) in Davis, Calif. The male parent is unknown. The open pollination occurred in May 2005 and the new *Hydrangea* was selected as a unique single plant in June 2008.

Asexual reproduction of the new cultivar was first accomplished by the Inventor using softwood stem cuttings in Davis, Calif. in June 2008. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Cotton Candy Two' as a unique cultivar of *Hydrangea macrophylla.*

1. 'Cotton Candy Two' exhibits a remontant (re-blooming) habit, blooming from May until frost.
2. 'Cotton Candy Two' exhibits lacecap type inflorescences with single sterile flowers surrounding a mass of fertile flowers.

3. 'Cotton Candy Two' exhibits flowers that are dark pink in color in color when grown with a soil PH of 7 or above.
4. 'Cotton Candy Two' exhibits sterile flowers with sepals that have serrated to crenated margins with a fine white edge on most sepals.
5. 'Cotton Candy Two' exhibits a 95% cutting rooting rate.

'Cotton Candy Two' differs from its female parent, 'Frau Reiko' in having a remontant blooming habit, in having a more compact plant habit, in having a much greater rooting rate, and in having 30% more branching. 'Cotton Candy Two' can be most closely compared to the cultivars 'Cotton Candy' (not patented) and 'Dancing Butterflies Improved'. 'Cotton Candy' differs from 'Cotton Candy Two' in having a higher rooting rate and in being more compact in habit. 'Dancing Butterflies Improved' differs from 'Cotton Candy Two' in having sterile flowers that are lighter pink in color and in having a wider white margin with entire margins on the sepals of the sterile flowers.

BRIEF DESCRIPTION OF THE DRAWINGS

The accompanying colored photographs illustrate the overall appearance and distinct characteristics of the new *Hydrangea* as grown in a greenhouse in Abbotsford, British Columbia. The photographs were taken of a one year-old plant of 'Cotton Candy Two' as grown in a 23-cm container with a soil pH of 7.

The photograph in FIG. 1 illustrates the foliage and compact form of 'Cotton Candy Two' and the photograph in FIG. 2 provides a close-up view of the inflorescences of 'Cotton Candy Two'. The colors in the photographs may differ slightly from the color values cited in the detailed botanical description, which accurately describe the colors of the new *Hydrangea.*

BOTANICAL DESCRIPTION OF THE PLANT

Figure 1:
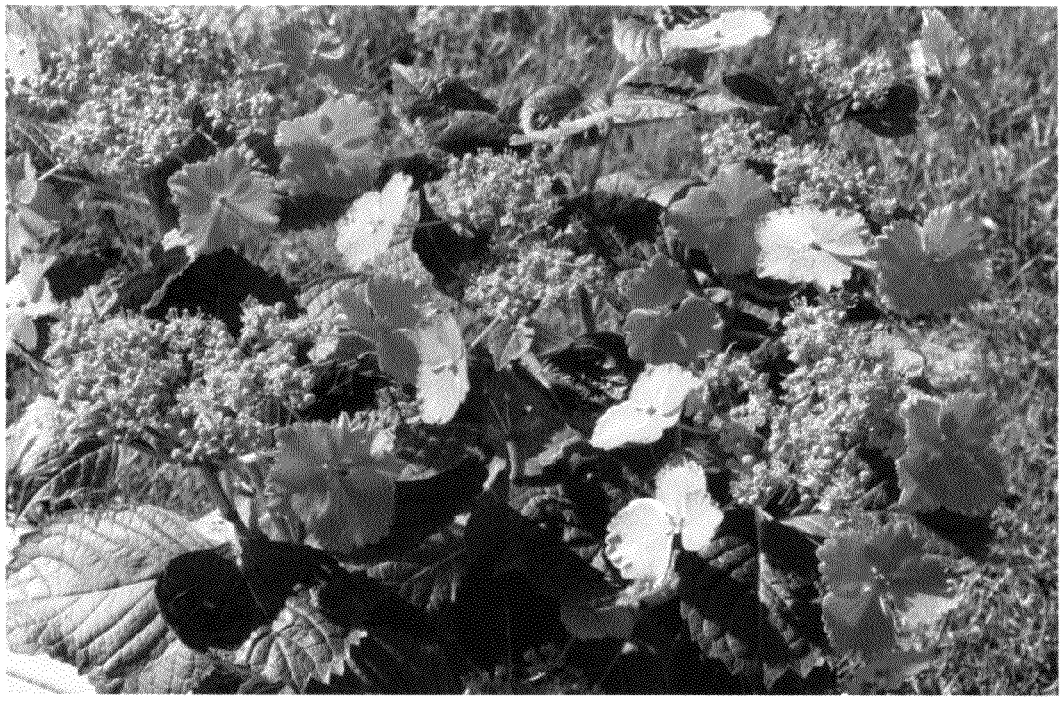
Figure 2:
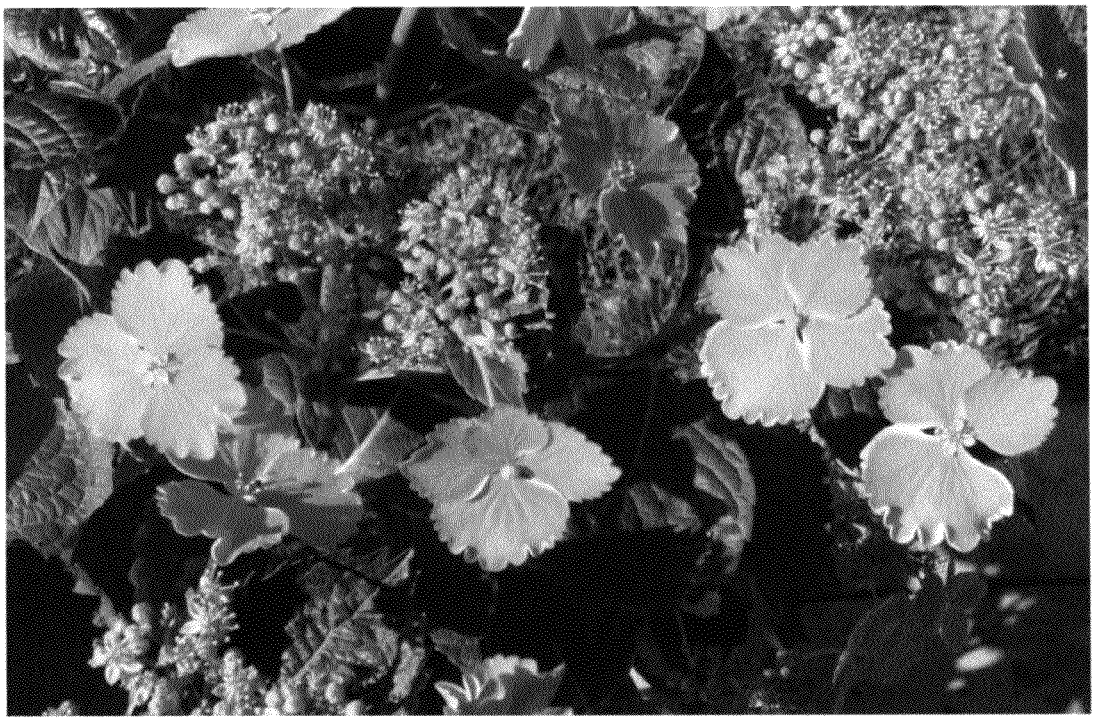

The following is a detailed description of one year-old plants of 'Cotton Candy Two' as grown in a greenhouse in 23-cm containers in Abbotsford, British Columbia. The detailed flower color data was taken from plants growing both under acidic conditions and alkaline conditions when differences exist. Phenotypic differences may be observed with variations in environmental, climatic, and cultural conditions. The color determination is in accordance with The 2001 R.H.S. Colour Chart of The Royal Horticultural Society, London, England, except where general color terms of ordinary dictionary significance are used.

General description:

*Blooming period*.—Re-blooming from May until frost from in Abbotsford, British Columbia, blooming will continue in winter with extended daylight.

*Plant type*.—Deciduous shrub, lacecap type *Hydrangea*.

*Plant habit*.—Compact mound.

*Height and spread*.—Reaches about 30 cm in height and 45 cm in width in a 23-cm container, up to 60 cm in height and width in a 3-gallon container.

*Hardiness*.—At least in U.S.D.A. Zones 5 to 9.

*Diseases resistance*.—Has been observed to be mildew free under the conditions grown.

*Root description*.—Fine.

Growth and propagation:

*Propagation*.—Softwood stem cuttings.

*Growth rate and vigor*.—Moderate to vigorous.

Stem description:

*Stem shape*.—Round, solid.

*Stem strength*.—Strong.

*Stem color*.—Young growth; 144B, mature growth; 198C.

*Stem size*.—Average of 20 cm (excluding inflorescence), average of 7 mm in diameter.

*Stem surface*.—Glabrous and glossy.

*Internode length*.—Average of 5 cm.

*Branching*.—An average of 12 lateral branches.

Foliage description:

*Leaf shape*.—Broadly oval.

*Leaf arrangement*.—Opposite.

*Leaf division*.—Simple.

*Leaf number*.—Average of 10 (5 pairs) per lateral branch.

*Leaf base*.—Cuneate.

*Leaf apex*.—Acuminate.

*Leaf margins*.—Serrate.

*Leaf venation*.—Pinnate, upper surface and lower surface; 139C.

*Leaf size*.—An average of 15 cm in length and 6 cm in width.

*Leaf attachment*.—Petiolate.

*Leaf surface*.—Smooth, moderately glossy.

*Leaf color*.—Young foliage upper surface; 144A, young foliage lower surface; 144B, mature foliage upper surface; 147A, mature foliage lower surface; 137B.

*Petioles*.—Average of 3 cm in length and 5 mm in diameter, 139C in color, glabrous surface.

Inflorescence description:

*Inflorescence type*.—Terminal compound corymb, lacecap in form comprised of a center region of fertile flowers surrounded by an outer ring of single sterile flowers.

*Lastingness of inflorescence*.—Persistent but color is retained for about 3 weeks.

*Inflorescence number*.—One per lateral or sublateral stem if pinched.

*Inflorescence size*.—Average of 10.5 cm in height and 20 cm in width.

*Flower number*.—Average of 100 sterile flowers and 200 fertile flowers per panicle.

*Flower fragrance*.—None.

*Flower aspect*.—Single sterile and fertile flowers arranged on terminal lacecap-type panicles, flowers face upright or outward.

*Flower size*.—Sterile flowers; average of 4 cm in diameter and 1 cm in depth, fertile flowers; average of 3 mm in diameter and 1 cm in depth.

*Flower type*.—Rotate.

*Flower buds*.—Sterile flowers; average of 6 mm in length and 45 mm in width prior to opening, ovate in shape, 144D in color prior to opening, fertile flowers; average of 4 mm in width and diameter, obovate to rounded in shape, 62B in color.

*Peduncles*.—Moderately strong, average of 5 cm in length and 4 mm in width, average angle of 10° from vertical, 66B in color.

*Pedicels*.—Held at a 20° angle from vertical, average of 2 cm in length and 2 mm in width on sterile flowers and an average of 4 mm in length and 1 mm in width on fertile flowers, 66B in color and glabrous surface on all flowers.

*Petals*.—Fertile flowers; average of 5, rotate in arrangement, ovate to lanceolate in shape, serrated margin, rounded apex, truncate base, average of 4 mm in length and 2 mm in width, surface is smooth and dull on both surfaces, color is 66B with thin margin (<1 mm) of 155A and fading to 67D, sterile flowers; closed into eye in under most conditions, an average of 4, eye is an average of 2 mm in diameter and depth, 65B in color, glabrous surface.

*Sepals*.—Sterile flowers; average of 4, broadly ovate in shape, an average of 2 cm in length and width, broadly acute to rounded apex, cuneate to rounded base, glabrous surface on upper and lower surface, serrated to crenated margins, color when grown with a soil pH of 7 color when flower opens upper and lower surface; 63A with a very thin margin of 155A, color when flower is fully open upper and lower surface; 68C with a thin edge of margin of 155A, fertile flowers; 6, ovate to lanceolate in shape, serrated margin, obtuse and retuse apex, attenuate base, average of 3 mm in length and 2 mm in width, surface is smooth and slightly glossy on both surfaces, color of upper and lower surface on open flower is 67A.

Reproductive organs: (fertile flowers):

*Stamens*.—Average of 15, anther is oblong in shape, 1 mm in length and 80B in color, filament is 5 mm in length, pollen is scarce in quantity and 200D in color.

*Pistils*.—Average of 4, average of 1 mm in length, stigma is rounded and 79A in color, style is an average of 1 mm in length and 79A in color, ovary is 145B in color.

*Fruit and seed*.—Has not been observed under the conditions tested to date.

It is claimed:

1. A new and distinct cultivar of *Hydrangea* plant named 'Cotton Candy Two' substantially as herein illustrated and described.

* * * * *